(12) United States Patent
Belbruno et al.

(10) Patent No.: US 9,260,683 B2
(45) Date of Patent: Feb. 16, 2016

(54) MOLECULARLY IMPRINTED POLYMER FOR WINE, METHOD OF PREPARING, AND USE OF SAME

(71) Applicants: The Trustees of Dartmouth College, Hanover, NH (US); Constellation Brands U.S. Operations, Inc., Canandaigua, NY (US)

(72) Inventors: Joseph J. Belbruno, Hanover, NH (US); Mark Kelm, Fresno, CA (US)

(73) Assignees: The Trustees of Dartmouth College, Hanover, NH (US); Constellation Brands U.S. Operations, Inc., Canandaigua, NY (US)

( * ) Notice: Subject to any disclaimer, the term of this patent is extended or adjusted under 35 U.S.C. 154(b) by 0 days.

(21) Appl. No.: 14/351,814

(22) PCT Filed: Oct. 15, 2012

(86) PCT No.: PCT/US2012/060248
§ 371 (c)(1),
(2) Date: Apr. 14, 2014

(87) PCT Pub. No.: WO2013/056226
PCT Pub. Date: Apr. 18, 2013

(65) Prior Publication Data
US 2014/0242237 A1   Aug. 28, 2014

Related U.S. Application Data

(60) Provisional application No. 61/546,739, filed on Oct. 13, 2011.

(51) Int. Cl.
| | |
|---|---|
| *C12H 1/056* | (2006.01) |
| *G01N 33/14* | (2006.01) |
| *C08L 33/12* | (2006.01) |
| *C08L 75/04* | (2006.01) |
| *C12G 1/00* | (2006.01) |
| *C08F 220/14* | (2006.01) |

(52) U.S. Cl.
CPC .............. *C12H 1/0424* (2013.01); *C08L 33/12* (2013.01); *C08L 75/04* (2013.02); *G01N 33/146* (2013.01); *C08F 220/14* (2013.01); *C12G 1/00* (2013.01)

(58) Field of Classification Search
CPC ...... C12H 1/0424; G01N 33/146; C12G 1/00; C08L 33/12; C08L 75/04; C08F 220/14
USPC ........... 426/422, 424, 490, 493, 496; 435/7.4; 436/164, 111, 71, 95, 96, 86, 20
See application file for complete search history.

(56) References Cited

U.S. PATENT DOCUMENTS

| | | |
|---|---|---|
| 6,127,154 A | 10/2000 | Mosbach et al. |
| 2002/0012727 A1 | 1/2002 | Leone |
| 2006/0102556 A1 | 5/2006 | Piletsky et al. |
| 2006/0292545 A1 | 12/2006 | Sellergren et al. |
| 2008/0264868 A1 | 10/2008 | Murray et al. |
| 2009/0035431 A1 | 2/2009 | Ebert |
| 2009/0281272 A1* | 11/2009 | Yilmaz et al. ................. 528/332 |
| 2010/0039124 A1 | 2/2010 | BelBruno et al. |
| 2010/0068820 A1 | 3/2010 | Meathrel et al. |
| 2010/0105076 A1* | 4/2010 | Perollier et al. ............... 435/7.4 |
| 2012/0196024 A1 | 8/2012 | Kelm |
| 2012/0214897 A1 | 8/2012 | Yiannikouris et al. |
| 2012/0291793 A1* | 11/2012 | Byrd et al. .................... 131/332 |
| 2014/0220706 A1* | 8/2014 | Belbruno ...................... 436/501 |
| 2014/0227795 A1 | 8/2014 | BelBruno |
| 2014/0242601 A1* | 8/2014 | Belbruno ...................... 435/7.1 |
| 2015/0232598 A1 | 8/2015 | BelBruno |

FOREIGN PATENT DOCUMENTS

| | | |
|---|---|---|
| EP | 1790714 | 5/2007 |
| GB | 2332529 | 6/1999 |
| WO | WO 2004/067578 | 8/2004 |
| WO | WO 2010/118523 | 10/2010 |
| WO | WO 2012/106265 | 8/2012 |
| WO | WO 2014/062632 | 4/2014 |

OTHER PUBLICATIONS

Winetech Scan. Feb. 2009. http://www.winetech.co.za/scan/WinetechScanFebruary2009.pdf.*
Teresa Garde-Cerdan et al. Abstract. Dec. 2008. American Journal of Enology and Viticulture. vol. 59, No. 4.*
Baggiani et al. (2007) "Molecularly imprinted solid-phase extraction method for the high-performance liquid in wine," *J. Chromatography* 1141(2):158-164.
BelBruno (2009) "Molecularly Imprinted Polymers: Artificial Receptors with Wide-Ranging Applications," *Micro and Nanosystems*. 1:163.
Belbruno et al. (Feb. 2, 2011) "Capacitive sensing of amino acids in molecularly imprinted nylon films," *Sensors and Actuators B*. 155(2):915-918.
Blahova et al. (2004) "The use of molecularly imprinted polymer for selective extraction of (+) 1 catechin," *J. Liquid Chromatography and Related Technologies*. 27(17):2715-2731.
Cacho et al. (2003) "Clean-up of triazines in vegetable extracts by molecularly-imprinted propazine-imprinted polymer," *Anal. Bioanal. Chem.* 376:491-496.
Campbell et al. (2009) "Surface Morphology of Spin-Coated Molecularly Imprinted Polymer Films," *Surf. Interface Analy.* 41:347-356.
Chapman (2004) "Yield Effects on 2-Methoxy-3-Isobutylpyrazine Concentration in Cabernet Sauvignon Using a Sold Phase Microextraction Gas Chromatography/Mass Spectrometry Method," *J. Agric. Food Chem.* 52:5431-5435.
Chapman et al. (2004) "Sensory Attributes of Cabernet Sauvignon Wines Made from Vines with Different Water Status," *Am. J. Enol. Vitic.* 55:325-334.

(Continued)

Primary Examiner — Anthony Weier
(74) *Attorney, Agent, or Firm* — Lathrop & Gage LLP

(57) ABSTRACT

Shown herein are compositions of, and methods of use for, molecularly imprinted polymers useful for extracting and/or detecting target molecule compounds of wine.

11 Claims, No Drawings

(56) References Cited

OTHER PUBLICATIONS

Chapuis et al. (2004) "Retention mechanism of analytes in the solid-phase from complex matrices," *J. Chromatography B*. 804(1):93-101.

Dela Cruz et al. (1999) "Molecular Imprinting of Methyl Pyrazines," *Analytical Letters*. 32(5):841-854.

Dirion et al. (2003) "Water-compatible molecularly imprinted polymers obtained Experimental Design," *J. Am. Chem. Soc.* 125(49):15101-15109.

Garde-Cerdan et al. (2008) "Molecularly Imprinted Polymer-Assisted Simple Clean-Up of 2,4,6-Trichloroanisole and Ethylphenols from Aged Red Wines," *Am. J. Enology. Viticulture*. 59(4):396-400 (2008).

Hashizume et al. (1999) "Grape maturity and light exposure affect berry methoxypyrazine concentration," *American J. Enology and Viticulture*. 50(2):194-198.

International Search Report in related International Patent Application No. PCT/US2013/064973, mailed Jan. 16, 2014.

International Search Report with Written Opinion in related International Patent Application No. PCT/US2012/060248, mailed Mar. 25, 2013.

International Search Report with Written Opinion in related International Patent Application No. PCT/US2012/023186, mailed Mar. 28, 2012.

Kotseridis et al. (1998) "Synthesis of labelled [$^2H_4$]β-damascenone, [$^2H_2$]$_{2\text{-}methoxy\text{-}3\text{-}isobutylpyrazine}$, [$^2H_3$]α-ionone, and [$^2H_3$]β-ionone, for quantification in grapes, juices and wines," *J. Chromatogr. A*. 824:71-78.

Kotseridis et al. (1999) "Quantitative Determination of 2-methoxy-3-isobutylpyrazine in Red Wines and Grapes of Bordeaux Using a Stable Isotope Dilution Assay," *J. Chromatogr. A*. 841:229-237.

Lele et al. (1999) "Molecularly imprinted polymer mimics of chymotrypsin: 1. Cooperative effects and substrate specificity," *Reactive and Functional Polymers*. 39(1):37-52.

Lin et al. (2003) "Molecularly imprinted polymeric beads for decaffeination," *J. Medical and Biological Engineering*. 23(2):53-56.

Maier et al. (2004) "Molecularly imprinted polymer-assisted sample clean-up of merits and limitations," *J. Chromatography B*. 804:103-111.

Molinelli et al. (2002) "Advanced solid phase extraction using molecularly imprinted polymers for the determination of quercetin in red wine," *J. Agric. Food Chem*. 50:1804-1808.

Mosbach et al. (1996) "The Emerging Technique of Molecular Imprinting and its Future Impact on Biotechnology," *Nat. Biotechnol*. 14:163-170.

Pap et al. (2004) "Binding assays with molecularly imprinted polymers—Why do they work?" *Journal of Chromatography B*. 804:167-172.

Polaskova et al. (2008) "Wine flavor: chemistry in a glass," *Chem. Soc. Rev*. 37:2478-2489.

Richter et al. (2006) "Processing and Morphology of Molecularly Imprinted Nylon Thin Films," *J. Appl. Polym. Sci*. 101:2919-2926.

Schneider (2010) "Aromatic and Phenolic Ripeness," Communication to the Pennsylvania Quality Association. *Schneider-Oenologie*. Germany.

Shea (1994) "Molecular imprinting of synthetic network polymers: The de novo synthesis of macromolecular binding and catalytic sites," *Trends Polym. Sci*. 2:166.

Sigma-Aldrich (1998) "Guide to Solid Phase Extraction," *Sigma-Aldrich*. Bulletin 910.

Sneshkoff et al. (2002) "An Improved Molecularly Imprinted Polymer Film for Recognition of Amino Acids," *J. Appl. Polym. Sci*. 86:3611-3615.

Tasselli et al. (2008) "Evaluation of molecularly imprinted membranes based on different acrylic copolymers," *J. Membrane Science*. 320(1-2):167-172.

Tse et al. (2010) "Molecularly imprinted polymers: synthetic receptors in bioanalysis," *Analytical and Bioanalytical Chemistry*. 398(6):2481-2492.

Wei et al. (2006) "Molecularly imprinted solid phase extraction in red wine," *Food Sci. Tech. Int*. 13(5):375-380.

Weiss et al. (2002) "Molecular Imprinting and Solid Phase Extraction of Flavonoid Compounds," *Bioseparation*. 10:379-387.

Wulff (1995) "Molecular Imprinting in Crosslinked Materials with the Aid of Molecular Templates Towards Artificial Antibodies," *Angew. Chem. Int. Ed*. 34:1812-1832.

Ye et al. (2008) "Molecular imprinting: synthetic materials as substitutes biological antibodies and receptors," *Chem. Mater*. 20:859-868.

\* cited by examiner

MOLECULARLY IMPRINTED POLYMER FOR WINE, METHOD OF PREPARING, AND USE OF SAME

RELATED APPLICATIONS

This application is a national phase application of International Application No. PCT/US2012/60248, filed on Oct. 15, 2012, which claims priority under 35 U.S.C. §119(e) to U.S. Provisional Patent Application No. 61/546,739 filed Oct. 13, 2011, the entire contents of which are incorporated herein by reference.

BACKGROUND

The complex flavor and nose of wine results from the presence of a wide range of organic molecules.[10,11] Not all of these organic molecules are desirable, at least not above a very critical concentration, in the finished product. While the components may, for the most part, be identified using highly sensitive analytical tools, the extraction of a single component of this mixture is difficult since the traditional liquid-liquid or solid phase extraction (SPE) materials and procedures will remove a broad spectrum of organics and could easily modify the characteristics of the wine.

SUMMARY

Imprinted polymers are prepared in the presence of the target molecule that interacts with the polymer network, in most applications, via hydrogen bonding interactions.[1,2] Other types of imprints, covalent or ionic for example, are possible, but less widely employed due to chemical difficulties removing the imprint molecule to prepare the material Imprints may also be created based on shape recognition of the template molecule. The molecularly imprinted polymers (MIPs) described herein use hydrogen bonding interactions between polymer and target molecule, as well as shape recognition. After the combined polymer/template network is established, thus forming a MIP network solution, the material is precipitated to form a MIP. The template (target molecule) is removed and the polymer retains a cavity that exhibits the ability to recognize the template by both shape and chemical interaction, with a high degree of selectivity.

Molecularly imprinted polymers have been widely used in chromatographic separations of drugs[3] and biological products.[4] MIPs may be produced as films or spherical particles for applications as separation agents.[5] In addition to the polymerization technique described above, there exists the application of applying solvent-soluble pre-formed polymers as the host matrix, creating a production technique allowing for rapid screening of potential matrices and allowing for the use of MIPs as sensing elements.[6-9]

The molecularly imprinted polymer materials described above are both highly specific and very effective. They may be targeted to a single molecule and reject binding, in a significant way, to any other molecule.

For example, the 2-isobutyl-3-methoxypyrazine molecule is an ideal candidate for a hydrogen bonding and cavity shape imprinted polymer material. The three potential hydrogen-binding sites on this molecule offer a significant chemical component to the specificity of the MIP. Alternatively, a proxy template, related to the true template molecule chemically or in shape such as 2-methoxypyrazine, may be substituted for the true template. Embodiments of methods for producing MIPs useful for the extraction of target molecules from wine include (1) phase inversion using a host polymer and (2) synthesis of a MIP from monomeric starting materials.

In an aspect, a MIP for detection of at least one target molecule component of wine is disclosed having at least one of polyurethane, poly(4-vinylphenol), or poly(methylmethacrylate), or co-polymers thereof. In an embodiment, the polymer is poly(4-vinylphenol)-co-poly(methylmethacrylate). In another embodiment, the MIP is in the form of a film or powder. In yet another embodiment, the MIP has a target molecule of one or more of 2-isobutyl-3-methoxypyrazine, 2-methoxypyrazine, 2-phenylethyl alcohol, guaiacol, or 4-methylguaiacol.

In an aspect, a method of preparing a MIP for detection of at least one target molecule of wine is disclosed, the method is dissolving a polymer in a first solvent to form a first solution, then adding a compound being substantially identical to the target molecule to the first solution to form a second solution, then mixing the second solution for a first period of time to form a MIP network solution, then recovering the MIP/compound composition from the MIP network solution, and then removing the compound from the MIP/compound composition to form the MIP. In an embodiment, the MIP/compound composition is recovered by precipitating the MIP network solution into a second solvent, filtering to recover the MIP/compound composition, and then adding a third solvent to the recovered MIP/compound composition to remove the compound to form the MIP. In another embodiment, the MIP/compound composition is recovered by casting the MIP network solution on a substrate, evaporating the first solvent to form an MIP film with the compound, placing the film in a second solvent to remove the compound, and drying the film to form the MIP. In another embodiment, the polymer is at least one of polyurethane, poly(4-vinylphenol), or poly(methylmethacrylate), or co-polymers thereof. In yet another embodiment, the polymer is poly(4-vinylphenol)-co-poly(methylmethacrylate).

In an embodiment of the methods herein, the "compound being substantially identical to the target molecule" is the target molecule itself, e.g., 2-isobutyl-3-methoxypyrazine, 2-methoxypyrazine, 2-phenylethyl alcohol, guaiacol, or 4-methylguaiacol.

In an embodiment, the first solvent is ethanol, toluene or DMF. In another embodiment, the second solvent is hexane or diethylether.

In another aspect, a method of preparing a MIP for detection of at least one target molecule of wine is disclosed that includes dissolving a monomer of one or more of urethane, 4-vinylphenol, or methylmethacrylate, as well as a compound being substantially identical to the target molecule, to a first solvent to form a first solution, then adding a cross-linking monomer to the first solution to form a second solution, then adding a polymerization initiator to the second solution to form a third solution, then recovering the resulting MIP/compound composition from the third solution, and then removing the compound to form the MIP. In an embodiment, the polymerization initiator is azobisisobutyronitrile.

In an embodiment, the cross-linking monomer is divinylbenzene, ethylene glycol, methylmethacrylate, methacrylic acid or dimethacrylate. In another embodiment,
the cross-linking monomer is divinylbenzene.

In another embodiment a MIP for the detection of at least one target molecule of wine is disclosed.

In an embodiment, a method of reducing the concentration of at least one target molecule of wine is disclosed that includes exposing the wine to a MIP that preferentially binds to a target molecule and/or homolog and/or analog thereof. In an embodiment, the target molecule is one or more of 2-isobutyl-3-methoxypyrazine, 2-methoxypyrazine, 2-phenylethyl alcohol, guaiacol, or 4-methylguaiacol.

DETAILED DESCRIPTION

The present disclosure provides methods for MIPs. Potential candidates for MIP polymers are those polymers that chemically interact with a target molecule or allow formation of shape recognition cavities. These MIP polymers (sometimes called polymer hosts) include, but are not limited to, at least one of polyurethane (PU), poly(4-vinylphenol) (P4VP), or poly(methylmethacrylate) (PMMA), or co-polymers thereof. It will be appreciated by those skilled in the art that modification of polymers and/or solvents allows for tuning the process of producing MIPs to the chemistry of a target molecule.

This disclosure describes a series of applications for the detection and/or measurement of contaminants in wine samples using MIPs produced with the disclosed methods. The MIPs are produced using solution chemistry in organic solvents for the detection of aqueous analytes, target molecules and/or homologs and analogs of target molecules. In this disclosure, a polymer host includes a structural component for a target analyte that is present during the formation of the MIP. For example, polyurethane is a shape/size recognition polymer or structural component.

In this disclosure, the target analytes (also referred to as target molecules) are in liquid form, either as a liquid or as one or more solids dissolved in liquid. The target molecules can include 2-isobutyl-3-methoxypyrazine (IBMP), 2-methoxypyrazine, 2-phenylethyl alcohol, guaiacol, or 4-methylguaiacol, odorants, tastants and tactile compounds, such as 2,4,6-trichloroanisole, 2-methylisoborneol, Geosmin (4,8a-dimethyldecalin-4a-ol), Methanethiol (methylmercaptan), Ethanethiol (ethylmercaptan), Dimethyl sulfide, Diethyl disulfide, Hydrogen sulfide, Acrolein (propenal), Acetic acid, Acetaldehyde, Amyl acetate, Diacetyl, Ethyl acetate, 4-ethylphenol, 4-ethylguaiacol, Vinyl-4-phenol, Isovaleric acid, 2-ethoxyhexa-3,5-diene, 2-acetyl-3,4,5,6-tetrahydropyridine, 2-acetyl-3,4,5,6-tetrahydropyridine, 2-ethyltetrahydropyridine, 2-acetyl-1-pyrrolene, Geraniol (3,7-Dimethylocta-2,6-diene-1-ol), Linalool (3,7-Dimethylocta-1,6-diene-3-ol), halogenated aromatics, trichlorophenol, tribromoanisole, 4,5-dichloroguaiacol, chlorovanillin, biogenic amines, histamine, tyramine, putrescine, phenylethylamine, Pronthocyanidins (a.k.a. condensed tannins), 4-aminoacetophenone, 1,1,6-trimethyl-1,2-dihydronaphthaline (TDN), 4-vinylguaiacol, cis-rose oxide, isopropylmethoxypyrazine, 2,3-butanedione, 3-hydroxybutanone, 2-mercaptoethanol, 1,1,6-trimethyl-1,2-dihydronaphthalene (TDN), $C_{13}$ norisoprenoid precursors of TDN (e.g. β-damascenone, β-ionone, vitispirane, actinidols, etc.), cis-3-Hexen-1-ol, 2-Methoxy-3,5-dimethylpyrazine and 2-secButyl-3-methoxypyrazine.

A typical MIP can involve non-covalent bonding, such as hydrogen bonding between the polymer host and the target molecule, or can exploit other electrostatic forces in conjunction with shape recognition, but the procedure is not limited to these variants. When the target molecule is removed, it creates an MIP cavity that is complementary in shape and functionality to the target molecule, which can rebind a target identical to the original target. The polymer host also has solvent compatibility with the target molecule, and is capable of forming a binding cavity around the target molecule.

The MIP materials are suitable for use as sensors that report the presence of the target analyte via, for example, a color change (either by a polymer incorporated chromophore, or an externally added reagent). Such a film can also be built into a capacitor to monitor dielectric changes due to the presence/absence of the target analyte. Films containing a polyelectrolyte, such as poly(amino acid), can be incorporated into a "chemiresistor" that monitors the presence of the analyte via conductivity changes.

MIP powders are useful for replacing generic SPE materials used in tubes as retention elements for liquid samples actively drawn through the tubes for a fixed period of time. In this case, the analytes adsorbed on the SPE materials can be extracted or placed directly into a sample port of an analytical technique including, for example, mass spectroscopy, gas chromatography, gas chromatography/liquid chromatography, high performance liquid chromatography, capillary electrophoresis, nuclear magnetic resonance spectroscopy, and various additional chromatographic spectroscopic techniques useful for subsequent separation and/or analysis.

SPE powders can also be used in a flow cell. For example, an SPE powder can be contained in the flow cell such that contaminated sample flows in, the contaminants are bound by the SPE powder, and a cleansed sample flows out that substantially lacks the target molecule. In another embodiment, SPE powders remove the target molecule and/or homologs/analogs thereof.

MIPs offer a significant advantage over generic SPE material because MIPs are designed to detect or remove a single contaminant, so that a separation phase prior to analysis is not necessary, and the amount extracted is simply quantified by a suitable analytical technique.

Having described several embodiments, it will be recognized by those skilled in the art that various modifications, alternative constructions, and equivalents may be used without departing from the spirit of the invention. Additionally, a number of well-known processes and elements have not been described in order to avoid unnecessary obscuring of the present invention. Accordingly, the above description should not be taken as limiting the scope of the invention.

General Experimental Protocols

Phase Inversion MIP Production:

The following procedure represents the typical ratio of materials used for MIP production and has been proportionally scaled up to 10 g quantities and can be scaled to 100 g or larger batches. Scaling follows the same proportions. The protocol starts with the dissolution of 1 g of polymer in 10 mL of solvent, typically absolute ethanol, toluene or dimethylformamide (depending upon the polymer), via magnetic stirring for approximately 30 minutes with nitrogen gas purging. A quantity of 0.5 g of target molecule (or a target molecule proxy) is added to this solution with constant stirring, the solution is again purged with nitrogen, sealed and stirred for 24 h at room temperature to form a host-target complex, this solution may be referred to as the MIP network solution. The MIP may be precipitated by the addition of the host-target solution to a quantity of 50 mL of a poor polymer solvent. The bulk polymer produced in this procedure may be ground and sieved to select a particular sized extraction material. The template is removed from the MIP by repeated washing with a liquid that solubilizes the target, but not the polymer. Typically, this requires at least five washings of 20 mL volume or several hours of Soxhlet extraction. The MIP particles are dried and are then ready for SPE applications.

Monomer Synthesized MIP:

To 12 mL of solvent, 1 mmol of target molecule is added along with 4 mmol of functional monomer (the monomer that chemically interacts with the target molecule). The mixture is stirred for 30 min. At this point 20 mmol of cross-linking monomer is added with 2 mmol of the polymerization initiator azobisisobutyronitrile. The reaction mixture, which may be referred to as a MIP network solution, is purged with nitrogen, sealed and placed in a 60° C. water bath for 24 h for polymerization to be completed. The bulk material produced in this synthesis is ground and sieved to the desired dimension and the template is removed by repeated washing as described above. After this step, the template is dried and ready for experimental SPE use.

Alternative Production Methods:

There are variants in the manner of precipitation of MIPs. If the polymer is a reactive polymer, it is possible to make the MIPs described here by exposing the solution to ultraviolet light for precipitation. It is also possible to precipitate the polymer by allowing the solvent to evaporate from the solution at room temperature while contained in a relatively flat holder. This method is ideal for producing a membrane, but can also be used to produce a granular solid that may be ground as described above.

Solid Phase Extraction:

The SPE process uses the single-tube processor sold by Sigma-Aldrich,[12] although any processing system may be used once the MIP is placed in a separation column. The MIP, produced from any of the methods described above is added to an empty SPE tube with a loading of at least 100 mg/mL of sample solution. The prepared tube is attached to the processor, the sample solution is added to the processor and constant pressure is applied to force the sample through the MIP, which binds the target specifically. Initial sample testing is with or without 12% ethanol with Nanopure water spiked with 200 ng/L or less of a target molecule. The upper limit of the target concentration in the synthetic sample is well above the usual quantity of these components in wine, but it allows a more stringent test of the ability to remove the molecules from the sample. The binding capacity of all of the MIPs is typically of the order of 3 mg of template bound per 100 mg of MIP, but the specific binding capacity of these MIPs is yet to be determined. The SPE-purified sample may then be analyzed quantitatively by GC-MS.

GC-MS Analysis of Target Molecules:

GC-MS analysis of 2-isobutyl-3-methoxypyrazine, for example, has been well defined by other researchers.[13-16] Similar methods are available for the other target molecules in the MIPs.

Specific Experimental Targets

MIPs have been produced with 2-isobutyl-3-methoxypyrazine and phenylethyl alcohol as the target molecules. MIPs can be produced for any flavor component of wine that may isolated in an analytical technique. The MIP, using these techniques, can employ a related molecule rather than the target molecule itself. This is because the MIP involves chemical forces in addition to shape. Only a fragment of the target molecule (the fragment that interacts chemically with the polymer host) is required to effectively imprint the polymer. For example, IBMP is very persistent and requires considerable effort to remove from the originally produced MIP. 2-methoxypyrazine has been substituted for IBMP and produced a MIP from which template is easily removed by diethylether and is extremely effective at sequestering IBMP. Moreover, the MIP is capable of removing all methoxypyrazines, including 2-isopropyl-3-methoxypyrazine, an unwanted component of wine, caused by the large population of ladybugs that exist in and near the vineyards. Similarly, a single MIP will be effective against both guaiacol and 4-methylguaiacol. Polyurethane (PU) membranes imprinted with IBMP, poly(4-vinylphenol) (P4VP) powders imprinted with both IBMP and 2-methoxypyrazine, poly(methylmethacrylate) (PMMA) powders imprinted with 2-methoxypyrazine, poly(methylmethacrylate-co-polymethylacrylic acid) (PMMA-co-PMAA) powders imprinted with 2-methoxypyrazine and poly(4-vinylphenol)-co-poly(methylmethacrylate) (P4VP-PMMA) powders imprinted with 2-methoxypyrazine have been made. Powders of poly(4-vinylphenol) imprinted with phenylethyl alcohol have also been made.

The solvent for P4VP and P4VP-PMMA MIPs is ethanol. For the PU membranes, the solvent is dimethylformamide. MIPs made from PMMA are produced in toluene.

Poly(4-vinylphenol) MIPs are precipitated with a two phase system consisting of 3× the original solution volume of distilled water with 2× the original solution volume of n-hexane. PMMA MIPs are precipitated in 5× the original volume of n-hexane. The P4VP-PMMA copolymer is precipitated in 5× the original solution volume of distilled water. All of the target molecules are removed by washing with n-hexane, hot distilled water or diethylether as described above followed by several washes with distilled water to remove any traces of organic molecule. The PU membranes are produced by solvent evaporation.

EXAMPLES

An unimprinted polymer, essentially pure P4VP that has undergone the same treatment as the MIP, does not remove IBMP from the aqueous solution. The MIP template with IBMP removes approximately 60% of the aqueous IBMP that passes through it. The removal is limited by the inability to extract all of the IBMP from the as-produced MIP. That is, the MIP retains some of the IBMP used in production and that IBMP slowly leaches into the sample that is passed through, essentially limiting the effectiveness of the MIP. The MIP produced with 2-methoxypyrazine removes more than 99% of the aqueous IBMP that passes through the SPE column. It does not remove, for example, the phenylethyl alcohol that is added to the synthetic mixture. Moreover, the MIP template with phenylethyl alcohol does not remove IBMP while proving effective for removing its target molecule.

A PMMA MIP templated with 2-methoxypyrazine removes 85% of the IBMP from a spiked sample of wine previously found to be devoid of IBMP and does not extract to any significant degree any of the other flavor components observed in a GC-MS scan of the unspiked wine sample.

Those skilled in the art will appreciate that the presently disclosed instrumentalities teach by way of example and not by limitation. Therefore, the matter contained in the above description or shown in the accompanying drawings should be interpreted as illustrative and not in a limiting sense. The following claims are intended to cover all generic and specific features described herein, as well as all statements of the scope of the present method and system, which, as a matter of language, might be said to fall therebetween.

REFERENCES CITED

1. L. Ye and K. Mosbach, "Molecular Imprinting: Synthetic Materials As Substitutes for Biological Antibodies and Receptors", Chem. Mater., 20, 859 (2008).
2. J. J. BelBruno, "Molecularly Imprinted Polymers: Artificial Receptors with Wide-Ranging Applications", Micro and Nanosystems, 1, 163 (2009).
3. G. Wulff, "Molecular Imprinting in Crosslinked Materials with the Aid of Molecular Templates—A way Towards Artificial Antibodies", Angew. Chem. Int. Ed., 34, 1812 (1995).

4. K. Mosbach and O. Ramstrom, "The Emerging Technique of Molecular Imprinting and its Future Impact on Biotechnology", Biotechnol., 14, 163 (1996).
5. K. J. Shea, "Molecular Imprinting of Synthetic Network Polymers: The DeNovo Synthesis of Macromolecular Binding and Catalytic Sites", Trends Polym. Sci., 2, 166 (1994).
6. K. Crabb, N. Shneskoff and J. J. BelBruno, "An Improved Molecularly Imprinted Polymer Film for Recognition of Amino Acids", J. Appl. Polym. Sci. 86, 3611 (2002).
7. A. Richter, U. J. Gibson, M. Nowicki and J. J. BelBruno, "Processing and Morphology of Molecularly Imprinted Nylon Thin Films", J. Appl. Polym. Sci, 101, 2919 (2006).
8. S. E. Campbell, M. Collins, Lie Xie, Lei and J. J. BelBruno "Surface Morphology of Spin-Coated Molecularly Imprinted Polymer Films", Surf. Interface Analy. 41, 347 (2009).
9. G. Zhang, J. J. BelBruno and U. J. Gibson, "Capacitive Sensing of Amino Acids in Molecularly Imprinted Polymers", submitted to Biosen. Bioelec., (2010).
10. P. Palaskova, J. Herszage and S. E. Ebeler, "Wine Flavor: Chemistry in a Glass", Chem. Soc. Rev., 37, 2478 (2008).
11. V. Schneider, "Aromatic and Phenolic Ripeness", Schneider-Oenologie, Germany.
12. Sigma-Aldrich, "Guide to Solid Phase Extraction". Bulletin 910.
13. D. M. Chapman, J. H. Thorngate, M. A. Matthews, J. X. Guinard and S. Ebeler, "Yield Effects on 2-Methoxy-3-Isobutylpyrazine Concentration in Cabernet Sauvignon Using A Sold Phase Microextraction Gas Chromatography/Mass Spectrometry Method", J. Agric. Food Chem., 52, 5431 (2004).
14. D. M. Chapman, G. Roby, S. Ebeler, J. X. Guinard and M. A. Matthews, "Sensory Attributes of Cabernet Sauvignon Wines Made from Vines with Different Water Status", Am. J. Enol. Vitic., 55, 325 (2004).
15. Y. Kotseridis, R. Baumes and G. Skouroumounis, "Synthesis of Labelled [2H4]-damascenone, [2H2]2-methoxy-3-isobutylpyrazine, [$^2H_3$]-ionone and [$^2H_3$]-ionone for Quantification in Grapes, Juices and Wines", J. Chromatogr. A, 824, 71 (1998).
16. Y. Kotseridis, R. Baumes, A. Bertand and G. Skouroumounis, "Quantitative Determination of 2-methoxy-3-isobutylpyrazine in Red Wines and Grapes of Bordeaux Using a Stable Isotope Dilution Assay", J. Chromatogr. A, 841, 229 (1999).

What is claimed is:

1. A molecularly imprinted polymer (MIP) for detection of at least one target molecule component of wine, comprising poly(4-vinylphenol)-co-poly(methylmethacrylate).

2. The MIP of claim 1, wherein the MIP is in the form of a film or powder.

3. The MIP of claim 1, further comprising the target molecule, wherein the target molecule is one or more of 2-isobutyl-3-methoxypyrazine, 2-methoxypyrazine, 2-phenylethyl alcohol, guaiacol, or 4-methylguaiacol.

4. A method of preparing a MIP for detection of at least one target molecule of wine, comprising:
   dissolving a polymer in a first solvent to form a first solution;
   adding a compound being substantially identical to the target molecule to the first solution to form a second solution;
   mixing the second solution for a first period of time to form a MIP network solution;
   recovering a MIP/compound composition from the MIP network solution; and
   removing the compound from the MIP/compound composition to form the MIP, wherein the MIP/compound composition is recovered by precipitating the MIP network solution into a second solvent and filtering to recover the MIP/compound composition, and then a third solvent is added to the recovered MIP/compound composition to remove the compound to form the MIP.

5. A method of preparing a MIP for detection of at least one target molecule of wine, comprising:
   dissolving a polymer in a first solvent to form a first solution;
   adding a compound being substantially identical to the target molecule to the first solution to form a second solution;
   mixing the second solution for a first period of time to form a MIP network solution;
   recovering a MIP/compound composition from the MIP network solution; and
   removing the compound from the MIP/compound composition to form the MIP, wherein polymer is at least one of polyurethane, poly(4-vinylphenol), or poly(methylmethacrylate), or co-polymers thereof.

6. The method of claim 5, wherein the polymer is poly(4-vinylphenol)-co-poly(methylmethacrylate).

7. The method of claim 5, wherein the first solvent is ethanol, toluene or DMF.

8. The method of claim 5, wherein the MIP/compound composition is recovered by precipitating the MIP network solution into a second solvent and the second solvent is hexane or diethylether.

9. A method of reducing the concentration of at least one target molecule of wine comprising exposing the wine to a MIP according to claim 1.

10. The method of claim 9, wherein the target molecule is one or more of 2-isobutyl-3-methoxypyrazine, 2-methoxypyrazine, 2-phenylethyl alcohol, guaiacol, or 4-methylguaiacol.

11. The method of claim 5, wherein the target molecule is one or more of 2-isobutyl-3-methoxypyrazine, 2-methoxypyrazine, 2-phenylethyl alcohol, guaiacol, or 4-methylguaiacol.

* * * * *